US009662906B2

(12) United States Patent
Kobayashi

(10) Patent No.: US 9,662,906 B2
(45) Date of Patent: May 30, 2017

(54) ILLUMINATION APPARATUS WITH HEAT RADIATION MEMBER

(71) Applicant: HOYA CANDEO OPTRONICS CORPORATION, Toda-shi, Saitama (JP)

(72) Inventor: Norio Kobayashi, Toda (JP)

(73) Assignee: HOYA CANDEO OPTRONICS CORPORATION, Toda-Shi, Saitama (JP)

( * ) Notice: Subject to any disclaimer, the term of this patent is extended or adjusted under 35 U.S.C. 154(b) by 0 days.

(21) Appl. No.: 15/151,532

(22) Filed: May 11, 2016

(65) Prior Publication Data

US 2016/0348887 A1 Dec. 1, 2016

(30) Foreign Application Priority Data

May 29, 2015 (JP) ................................ 2015-110936

(51) Int. Cl.
*A61N 5/00* (2006.01)
*B41J 11/00* (2006.01)

(52) U.S. Cl.
CPC .................................. *B41J 11/002* (2013.01)

(58) Field of Classification Search
CPC ...... F21V 29/00; F21V 29/002; F21V 29/004; F21V 29/006; F21V 29/02; F21V 29/503; F21V 29/57; F21V 29/60; F21V 29/67; F21V 29/74; F21V 29/75; F21V 29/76; F21V 29/763; F21V 29/767; F21V 29/77; F21V 29/773; F21V 29/777; F21V 29/78
USPC ..... 250/492.1, 493.1, 494.1, 453.11, 454.11, 250/455.11
See application file for complete search history.

(56) References Cited

U.S. PATENT DOCUMENTS

2006/0082271 A1* 4/2006 Lee ........................ F21V 29/02 313/35
2013/0003392 A1* 1/2013 Tsai ........................ F21V 29/20 362/373
2015/0221844 A1* 8/2015 Tahara .................. H01L 27/153 250/492.1

FOREIGN PATENT DOCUMENTS

JP 2013-252720 A 12/2013

* cited by examiner

*Primary Examiner* — Jason McCormack
(74) *Attorney, Agent, or Firm* — Rabin & Berdo, P.C.

(57) ABSTRACT

A thin-type light illuminating apparatus with a heat radiation member having high heat radiation efficiency. The light illuminating apparatus for illuminating light in line shape extending in a first direction on an illumination surface includes an elongated substrate extending in the first direction, a plurality of light emitting diode (LED) light sources on the substrate, a heat transfer pipe extending in a second direction, and configured to transfer heat generated from the LED light sources in the second direction, a heat radiation sink having a plurality of heat radiation fins protruding in a third direction, an illuminator having a thin box shape and configured to house the substrate, the heat transfer pipe and the heat radiation sink and to form a wind tunnel, and a centrifugal fan in the second direction between the substrate and the heat radiation sink, and configured to draw air from outside into the wind tunnel.

14 Claims, 8 Drawing Sheets

ILLUMINATION APPARATUS WITH HEAT RADIATION MEMBER

TECHNICAL FIELD

The present disclosure relates to a light illuminating apparatus that has a light emitting diode (LED) as a light source and illuminates light in line shape, and more particularly, a light illuminating apparatus having a heat radiation member which radiates heat generated from an LED.

BACKGROUND ART

Conventionally, a printing apparatus designed to print using an ultraviolet (UV) ink which is cured by illumination with UV light is known. This printing apparatus discharges an ink onto a medium from nozzles of heads, and then illuminates UV light onto dots formed on the medium. By the illumination with UV light, the dots are cured and settled down on the medium, thereby achieving good printing on a medium that cannot absorb a liquid. This printing apparatus is described in, for example, Patent Literature 1.

Patent Literature 1 discloses a printing apparatus comprising a transport unit to transport a printing medium, six heads arranged in the transportation direction to respectively discharge color inks of cyan, magenta, yellow, black, orange, and green, six illumination units for pre-curing arranged between each head on the downstream side in the transportation direction to pre-cure (peening) the dot inks discharged onto the printing medium from each head, and an illumination unit for curing to cure the dot inks which are settled down on the printing medium. The printing apparatus described in Patent Literature 1 cures the dot inks through two steps, pre-curing and curing, to prevent any blur between color inks or dot spreads.

The illumination units for pre-curing described in Patent Literature 1 are a so-called UV light illumination apparatus disposed above the printing medium to illuminate UV light onto the printing medium, and illuminate UV light in line shape along the widthwise direction of the printing medium. By the request for lightweight and compact design of the printing apparatus itself, the illumination units for pre-curing use a light emitting diode (LED) as a light source, and a plurality of LEDs is arranged along the widthwise direction of the printing medium.

RELATED LITERATURES

Patent Literature

Japanese Unexamined Patent Publication No. 2013-252720

DISCLOSURE

Technical Problem

Like the illumination units for pre-curing described in Patent Literature 1, when a light emitting diode (LED) is used as a light source, because most of the fed power turns into heat, there is a problem with reduced light emitting efficiency and short life caused by heat generated from the LED itself. Also, like the illumination units for pre-curing, in the case of an apparatus with a plurality of LEDs, this problem is more serious due to the increased number of LEDs acting as a source of heat. For this reason, a light illuminating apparatus using an LED as a light source generally uses a heat radiation member such as a heat sink to inhibit the heat generation from the LED.

To inhibit the heat generation from the LED, it is effective to use a heat radiation member such as a heat sink. However, to efficiently radiate the heat from the LED, the heat radiation member needs to have as large a surface area as possible, and if the heat radiation member increases in size, there is a problem with the increased size of the entire apparatus. Particularly, like the illumination units for pre-curing of Patent Literature 1, when a large-scale heat radiation member is applied to the light illuminating apparatus arranged between each head, the distance between each head should be increased, and the problem with the increased weight and size of the printing apparatus itself becomes more serious.

To address the above issue, the present disclosure is directed to providing a thin-type light illuminating apparatus with a heat radiation member having high heat radiation efficiency.

Technical Solution

To achieve the above object, a light illuminating apparatus of the present disclosure is a light illuminating apparatus for illuminating light in line shape extending in a first direction on an illumination surface, and includes an elongated substrate extending in the first direction, a plurality of light emitting diode (LED) light sources placed and arranged on a surface of the substrate at a predetermined interval along the first direction, and configured to emit the light in line shape, a heat transfer means of which at least a part is in contact with the substrate, the heat transfer means extending in a second direction perpendicular to the first direction from the substrate, and configured to transfer heat generated from the LED light sources in the second direction, a heat radiation means having a plurality of heat radiation fins protruding in a third direction perpendicular to the first direction and the second direction from the heat transfer means and installed to extend in the second direction, an illuminator having a thin box shape in the third direction and configured to house the substrate, the heat transfer means and the heat radiation means and to form a wind tunnel at an area in which the heat radiation means is formed, and a centrifugal fan placed in the second direction between the substrate and the heat radiation means, and configured to draw air from the outside into the wind tunnel to generate an air current of the second direction within the wind tunnel.

By this configuration, because heat generated from the LED light sources is transferred in the second direction and irradiated, a thin light illuminating apparatus in the third direction is realized.

Also, the illuminator may have an air intake port on at least one of one surface facing an imaginary surface formed by the ends of the plurality of heat radiation fins and the other surface facing the first direction, the air intake port configured to take in air from the outside, and the centrifugal fan may be configured to take in air from the air intake port.

Also, the first direction width of the heat transfer means may be approximately equal to the first direction width of the substrate.

Also, a bottom part of the heat transfer means may be bent in a shape of letter L, and the bottom part may be thermally coupled with the other surface of the substrate.

Also, the light illuminating apparatus may further include a support block which is thermally coupled with the other surface of the substrate and supports the substrate, the heat transfer means may include a first heat transfer means, and a second heat transfer means smaller than the first heat transfer means in the second direction, the heat radiation means may include a first heat sink having the heat radiation fins on the first heat transfer means, and a second heat sink having the heat radiation fins on the second heat transfer means, and the support block may be installed to be inserted by a bottom part of the first heat transfer means and a bottom part of the second heat transfer means.

Also, a driving circuit may be provided between the centrifugal fan and the heat radiation means to drive the LED light sources.

Also, the heat transfer means may include a plate-shaped heat pipe extending in the first direction and the second direction.

Also, the heat transfer means may include a plurality of rod-shaped heat pipes arranged in the first direction and extending in the second direction.

Also, the substrate may be placed on a plane defined by the first direction and the third direction, and optic axes of each of the LED light sources may face an opposite direction to the second direction. Also, in this case, the LED light sources may be arranged in N rows along the third direction when the substrate is planarized, in which N is an integer larger than or equal to 2.

Also, the substrate may be placed on a plane defined by the first direction and the second direction, and optic axes of each of the LED light sources may face the third direction. In this case, the LED light sources may be arranged in N rows along the second direction when the substrate is planarized, in which N is an integer larger than or equal to 2.

Also, the centrifugal fan may include a first centrifugal fan having a fan which rotates in a counterclockwise direction, and a second centrifugal fan having a fan which rotates in a clockwise direction, and the first centrifugal fan and the second centrifugal fan may be placed and arranged in the first direction.

Also, the light may be light including a wavelength used for an ultraviolet curing resin.

Advantageous Effects

As hereinabove described, according to the present disclosure, a thin-type light illuminating apparatus with a heat radiation member having high heat radiation efficiency is realized.

[Detailed Description of Main Elements]

Figure 1:
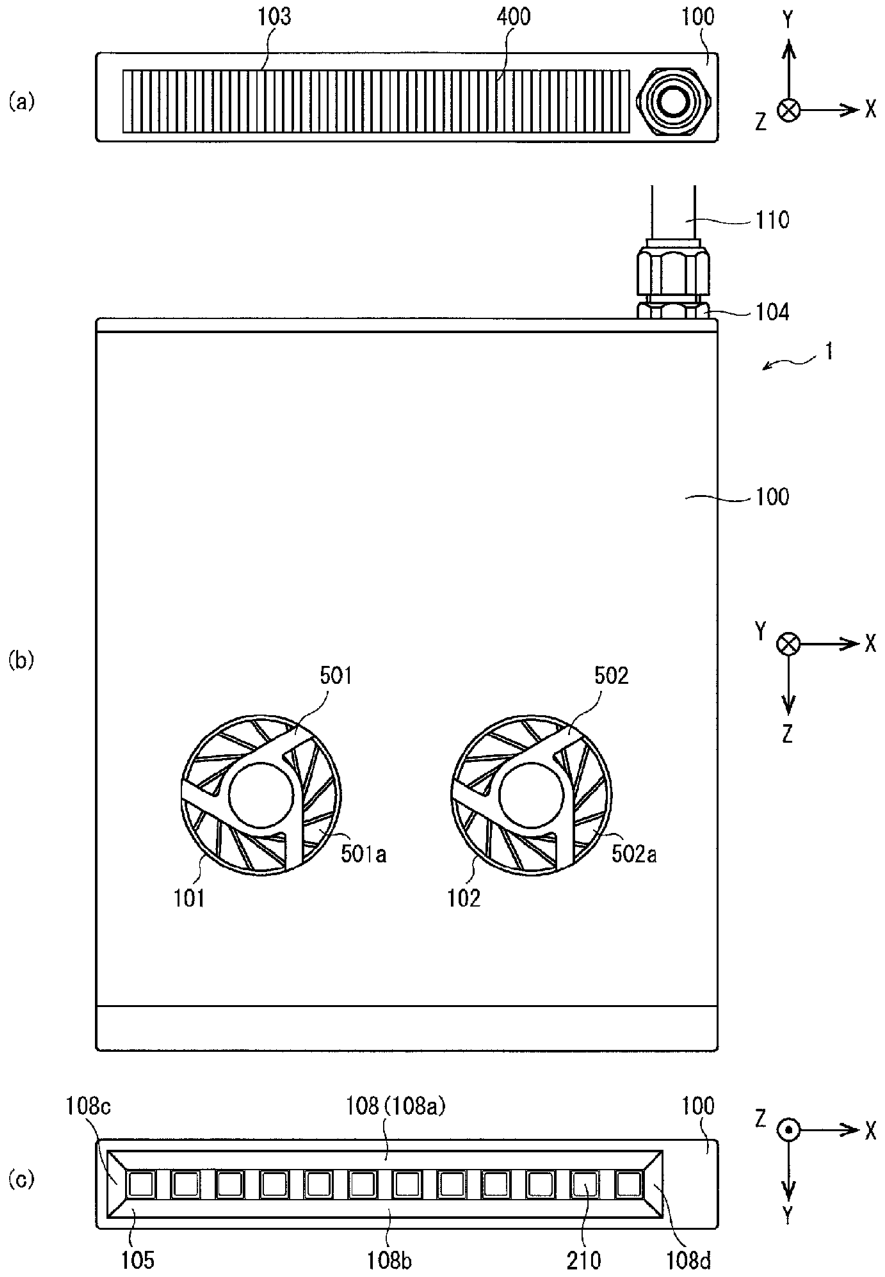
FIG. 1 is a diagram illustrating the appearance of a light illuminating apparatus according to a first embodiment of the present disclosure.

| | |
|---|---|
| 1, 1A, 1B, 1C, 1D Light illuminating apparatus | |
| 100 Case | 101, 102 Air intake port |
| 103 Air exhaust port | 104 Connector |
| 105 Window | 106 Internal wiring cable |
| 107 Support plate | 107A Support block |
| 108 Reflection member | 109 Support member |
| 110 Cable | 200 Light source unit |
| 205 Substrate | 210 LED device |
| 400 Heat radiation member | 410, 410A, 440, 460 Heat pipe |
| 410a Planar part | 410b Bent part |
| 412 Rod-shaped heat pipe | 430 Heat sink |
| 430a Heat radiation fin | 501, 502, 501C Centrifugal fan |
| 501D, 502D Centrifugal turbo fan | 501a, 502a Air intake port |
| 501b, 502b Air exhaust port | 600 LED driving circuit |

BEST MODE

Hereinafter, the embodiments of the present disclosure will be described in detail with reference to accompanying drawings. Also, in the drawings, the same or equivalent parts are assigned the same reference numerals and their description is not repeated.

First Embodiment

FIG. 1 is a diagram illustrating the appearance of a light illuminating apparatus 1 according to a first embodiment of the present disclosure, and FIG. 1(*a*) is a top view of the light illuminating apparatus 1. Also, FIG. 1(*b*) is a front view of the light illuminating apparatus 1, and FIG. 1(*c*) is a bottom view of the light illuminating apparatus 1. The light illuminating apparatus 1 of this embodiment is a light source apparatus mounted in a printing apparatus to cure an ultraviolet (UV) curing ink or UV curing resin, and for example, the light illuminating apparatus 1 is disposed above an object and sheds UV light in line shape upon the object. Also, in the specification, as shown in the coordinates of FIG. 1, a direction in which light emitting diode (LED) devices 210 to be described later emits UV light is defined as a Z-axis direction, an arrangement direction of LED devices 210 as an X-axis direction, and a direction perpendicular to the Z-axis direction and the X-axis direction as a Y-axis direction.

As shown in FIG. 1, the light illuminating apparatus 1 of this embodiment has a thin box-shaped case 100 (illuminator) which houses a light source unit 200 or a heat radiation member 400 therein. The case 100 has, on the bottom, a window 105 of glass through which UV light is emitted. Also, the case 100 has air intake ports 101 and 102 to take in air from the outside on a front surface (a surface facing an imaginary surface formed by the ends of a plurality of heat radiation fins 430*a* described later), and an air exhaust port 103 to exhaust air from the case 100 on the top. Also, a connector 104 for supplying power source to the light illuminating apparatus 1 is installed on the top of the case 100, and the connector 104 and a power supply (not shown) are connected with a cable 110 to supply a power source to the light illuminating apparatus 1.

Figure 2:
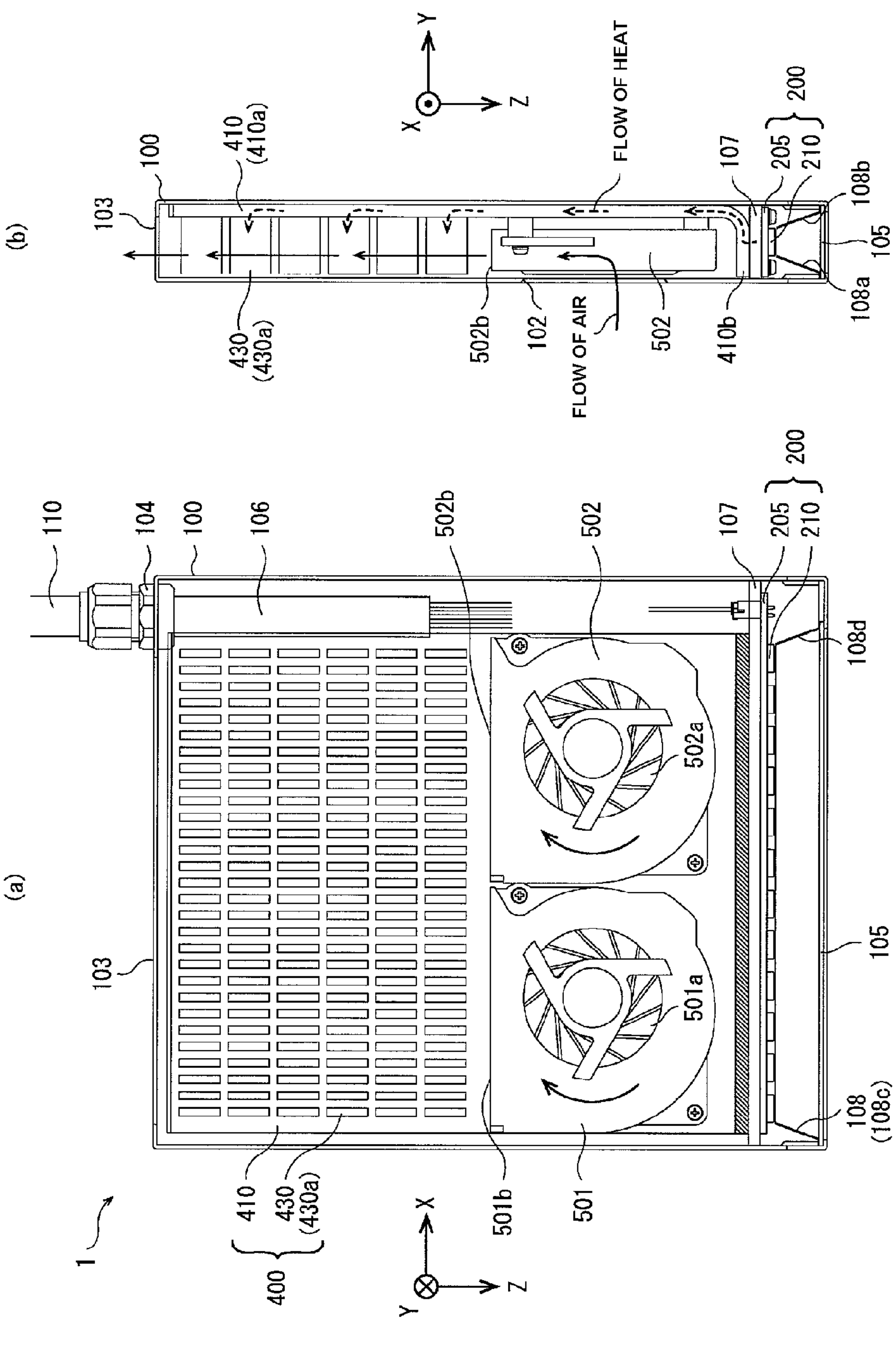
FIG. 2 is a diagram illustrating the internal structure of a light illuminating apparatus according to a first embodiment of the present disclosure.

FIG. 2 is a diagram illustrating the internal structure of the light illuminating apparatus 1 according to the embodiment of the present disclosure, and FIG. 2(*a*) is a front projection diagram of the light illuminating apparatus 1 when viewed from the front. Also, FIG. 2(*b*) is a side projection diagram of the light illuminating apparatus 1 when viewed from the right side. Also, in FIG. 2(*b*), an internal wiring cable 106 of FIG. 2(*a*) has been omitted for clarity.

As shown in FIG. 2, the light illuminating apparatus 1 of this embodiment has the light source unit 200, the heat radiation member 400, and two centrifugal fans 501 and 502 within the case 100.

As shown in FIGS. 2(*a*) and (*b*), the light source unit 200 has a substrate 205 with a rectangular shape parallel to the X-axis direction and the Y-axis direction and twelve LED devices 210 having the same characteristics, and is fixed on one surface (a surface facing the bottom surface of the case 100) of a support plate 107 made of metal (e.g., copper and aluminum) extending in the X-axis direction within the case 100.

The twelve LED devices 210 are arranged in a line on the surface of the substrate 205 at a predetermined interval in the X-axis direction with optic axes parallel to the Z-axis direction, and are electrically connected to the substrate 205. Also, the substrate 205 is electrically connected to a part of the internal wiring cable 106 extending from the connector 104, and a drive current from the power supply (not shown) is supplied to each LED device 210. When the drive current is supplied to each LED device 210, an amount of UV light (for example, wavelength 365 nm) corresponding to the drive current is emitted from each LED device 210, and UV light in line shape parallel to the X-axis direction is emitted from the light source unit 200.

As shown in FIGS. 1 and 2, in this embodiment, a reflection member 108 is installed between the light source unit 200 and the window 105. The reflection member 108 has four mirror surfaces 108*a*, 108*b*, 108*c* and 108*d* arranged to surround the light path of the twelve LED devices 210. Each mirror surface 108*a*, 108*b*, 108*c* and 108*d* spreads outward in the emission direction of UV light (i.e., Z-axis direction), and thereby, regulates the light path of UV light emitted at a predetermined divergence angle from each LED device 210, and guides a predetermined intensity of UV light to be illuminated onto a desired illumination area approximately vertically. Also, UV light guided by the reflection member 108 is emitted from the light illuminating apparatus 1 through the window 105. Also, the drive current supplied to each LED device 210 is tuned to allow each LED device 210 of this embodiment to emit an approximately uniform amount of UV light, and UV light in line shape emitted from the light source unit 200 has an approximately uniform light distribution in the X-axis direction.

The heat radiation member 400 is a member which radiates heat generated from the light source unit 200. The heat radiation member 400 of this embodiment is fixed to the support plate 107 such that one end part of the heat radiation member 400 comes into contact with the other end surface of the support plate 107 (a surface facing the top of the case 100), and includes a heat pipe 410 (heat transfer means) to transfer heat generated from each LED device 210, and a heat sink 430 (heat radiation means) composed of a plurality of heat radiation fins 430*a* fixed to the heat pipe 410 such that the heat radiation fins 430*a* are in close contact with the heat pipe 410 (FIGS. 2(*a*) and (*b*)).

The heat pipe 410 is a plate-shaped member of metal (e.g., metals such as copper, aluminum, iron, and magnesium, or alloys thereof) having an internal space (not shown in FIG. 2) filled with a working fluid (e.g., water, alcohol, and ammonia) and sealed under reduced pressure. As shown in FIG. 2(*b*), the heat pipe 410 of this embodiment is bent in the shape of letter L in cross section such that a substrate 205 side end part conforms to the other surface of the support plate 107, and has a planar part 410*a* parallel to the X-Z planes and a bent part 410*b* parallel to the X-Y planes. The bent part 410*b* is fixed on the other surface of the support plate 107 by a fastener or adhesive (not shown) such that the bent part 410*b* is in contact with the other surface of the support plate 107, and is thermally coupled with the substrate 205.

Figure 3:
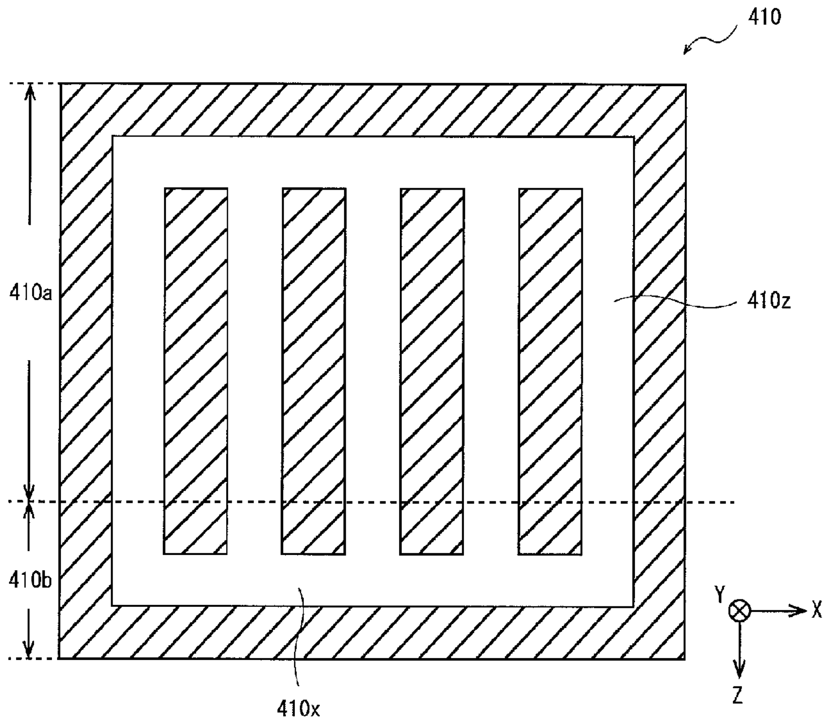
FIG. 3 is a cross-sectional view illustrating an internal space of a heat pipe provided in a light illuminating apparatus according to a first embodiment of the present disclosure.

FIG. 3 is a cross-sectional view illustrating the internal space of the heat pipe 410 of this embodiment. Also, in FIG. 3, for convenience of description, the bent part 410*b* is shown on the same plane as the planar part 410*a*. As shown in FIG. 3, the internal space of the heat pipe 410 of this embodiment extends in the Z-axis direction within the planar part 410*a* continuously from the bent part 410*b*, and includes a plurality of pipe-shaped spaces 410*z* arranged at a predetermined interval in the X-axis direction and two pipe-shaped spaces 410*x* connecting each space 410*z* in the X-axis direction. Also, as the working fluid moves within the space 410*z*, heat is transferred in the Z-axis direction (the opposite direction to the direction in which UV light is emitted) from the bent part 410*b* (described in detail later). Also, in this embodiment, the working fluid also moves in the X-axis direction through the space 410*x*, so the heat pipe 410 transfers heat approximately uniformly along the X-axis direction and the Z-axis direction (i.e., along the X-Z planes).

The plurality of heat radiation fins 430*a* of the heat sink 430 is a member of metal (e.g., metals such as copper, aluminum, iron, and magnesium, or alloys thereof) with a rectangular plate shape. As shown in FIGS. 2(*a*) and (*b*), each heat radiation fin 430*a* of this embodiment is welded to one side surface (a surface on the side where the bent part 410*b* is bent) of the planar part 410*a* of the heat pipe 410, so that the heat radiation fins 430*a* are installed erect to protrude in the Y-axis direction from the planar part 410*a*, to radiate the heat transferred to the heat pipe 410 in the air. Also, as will be described in detail later, in this embodiment, air is taken into the case 100 from the outside by the centrifugal fans 501 and 502 and an air current of the Z-axis direction is generated to allow the taken air to flow along the surfaces of the heat radiation fins 430*a*, and the heat radiation fins 430*a* are installed to extend in the Z-axis direction. Also, the heat radiation fins 430*a* of this embodiment include multiple (six) split heat radiation fins formed in the Z-axis direction. Also, a protrusion amount of the heat radiation fins 430*a* (the size of the heat radiation fins 430*a*) is set as much as the heat radiation fins 430*a* do not come into contact with the inner surface of the case 100.

When the drive current flows in each LED device 210 and UV light is emitted from each LED device 210, the temperature rises by self-heat generation of the LED device 210, and heat generated from each LED device 210 is transferred by conduction (moves) to the bent part 410*b* of the heat pipe 410 through the substrate 205 and the support plate 107 quickly. Also, when heat moves to the bent part 410*b* of the heat pipe 410, the working fluid within the heat pipe 410 absorbs the heat and evaporates, and the working fluid vapor moves through the internal space, so the heat in the bent part 410_b_ moves to the planar part 410_a_. Also, the heat moved to the planar part 410_a_ moves to the plurality of heat radiation fins 430_a_ combined with the planar part 410_a_, and is radiated in the air from each heat radiation fin 430_a_. When the heat is radiated from each heat radiation fin 430_a_, the temperature of the planar part 410_a_ is reduced, and the working fluid vapor within the planar part 410_a_ is cooled and returns to a liquid which moves to the bent part 410_b_. Also, the working fluid having moved to the bent part 410_b_ is used to absorb heat newly conducted through the substrate 205 and the support plate 107.

As described above, in this embodiment, the working fluid within the heat pipe 410 circulates between the bent part 410_b_ and the planar part 410_a_, so that heat generated from each LED device 210 moves to the heat radiation fins 430_a_ quickly, and is efficiently radiated in the air from the heat radiation fins 430_a_.

The centrifugal fans 501 and 502 are a so-called centrifugal sirocco fan having a rotation axis in the Y-axis direction, and take in air in the Y-axis direction from the outside and sends air in the centrifugal direction. When the centrifugal fans 501 and 502 rotate, an air current of the Z-axis direction is generated within the case 100, and air that became hot is discharged outside by the heat radiation fins 430_a_ and each heat radiation fin 430_a_ is cooled. As shown in FIGS. 2(_a_) and (_b_), the centrifugal fans 501 and 502 of this embodiment are arranged along the X-axis direction in a space between the light source unit 200 and the heat radiation fins 430_a_ on the planar part 410_a_ of the heat pipe 410. Air intake ports 501_a_ and 502_a_ of the centrifugal fans 501 and 502 are respectively installed at locations corresponding to the air intake ports 101 and 102 (FIG. 1), and air exhaust ports 501_b_ and 502_b_ face the direction of the air exhaust port 103. Thus, when the centrifugal fans 501 and 502 rotate, the outside air is taken into the case 100 through the air intake ports 101 and 102, and air within the case 100 is exhausted from the air exhaust port 103. That is, an air current (flow of air) indicated by solid arrows in FIG. 2(_b_) is generated in the case 100, and air taken into the case 100 from the air intake ports 101 and 102 flows in a space surrounded by the heat pipe 410 and the case 100 (i.e., a space in which the heat radiation fins 430_a_ are installed) in the Z-axis direction (the opposite direction to the direction in which UV light is emitted). By this reason, heat (indicated by dotted arrows in FIG. 2(_b_)) generated from each LED device 210 and transferred to each heat radiation fin 430_a_ through the substrate 205, the support plate 107, and the heat pipe 410 is irradiated in the air around each heat radiation fin 430_a_ and discharged to the outside with the movement of air.

As described above, in this embodiment, the case 100 and the heat pipe 410 form a sort of wind tunnel and define a space in which an air current flows, thereby efficiently cooling each heat radiation fin 430_a_. Also, in this embodiment, the centrifugal fans 501 and 502 of thin type are employed in which the direction of the air intake ports 501_a_ and 502_a_ is perpendicular to the direction of the air exhaust ports 501_b_ and 502_b_, and the centrifugal fans 501 and 502 are arranged between the light source unit 200 and the heat radiation fins 430_a_, thereby efficiently cooling each heat radiation fin 430_a_ and achieving a thickness reduction of the light illuminating apparatus 1.

Hereinabove this embodiment has been described, and the present disclosure is not limited to the above configuration, and various modifications can be made within the scope of the technical spirit of the present disclosure.

For example, although this embodiment shows that the substrate 205 and the heat pipe 410 are bonded through the support plate 107, the support plate 107 is not indispensable, and the substrate 205 and the heat pipe 410 may be directly bonded to each other.

Also, although the light illuminating apparatus 1 of this embodiment illuminates UV light in the Z-axis direction from the bottom of the case 100, for example, the substrate 205 may be placed parallel to the X-Z planes, and configured to illuminate UV light in the Y-axis direction from the front or rear of the case 100. In this case, the heat pipe 410 does not need to have the bent part 410_b_, and a plate-shaped heat pipe having only the planar part 410_a_ may be applied.

Also, although the light illuminating apparatus 1 of this embodiment is an apparatus for illuminating UV light, the present disclosure is not limited thereto and may be also applied to an apparatus for illuminating light of other wavelength bands (e.g., visible light including white light, infrared light, etc.).

Also, although this embodiment shows that each heat radiation fin 430_a_ is directly welded to the planar part 410_a_ of the heat pipe 410, the plurality of heat radiation fins 430_a_ may be formed on a base, and the corresponding base may be fixed to the planar part 410_a_. Also, in this case, a high thermal conductivity graphite sheet may be installed between the heat pipe 410 and the base, or silicone grease may be applied to achieve closer contact therebetween.

Also, although each heat radiation fin 430_a_ of this embodiment is installed to extend in the Z-axis direction, because the centrifugal fans 501 and 502 send air in the centrifugal direction, the direction of the wind (the direction of the air current) and the direction in which the heat radiation fins 430_a_ is installed to extend do not necessarily match depending on the location of each heat radiation fin 430_a_. Thus, to match the direction of the wind (the direction of the air current) and the direction in which the heat radiation fins 430_a_ are installed to extend, each heat radiation fin 430_a_ may be arranged obliquely to the Z-axis direction depending on the location of each heat radiation fin 430_a_. By this configuration, the direction in which each heat radiation fin 430_a_ is installed to extend is parallel to the direction of the wind (the direction of the air current), thereby efficiently cooling.

Also, although this embodiment shows the use of two centrifugal fans 501 and 502, any number of centrifugal fans to generate an air current in the wind tunnel formed by the case 100 and the heat pipe 410 may be provided, and one centrifugal fan may be provided and three or more centrifugal fans may be provided.

Also, although this embodiment shows that twelve LED devices 210 are arranged in a line on the substrate 205, the number of LED devices 210 may be properly changed based on the specification, and the LED devices 210 may be arranged in N rows (N is an integer larger than or equal to 2) along the Y-axis direction.

Figure 4:
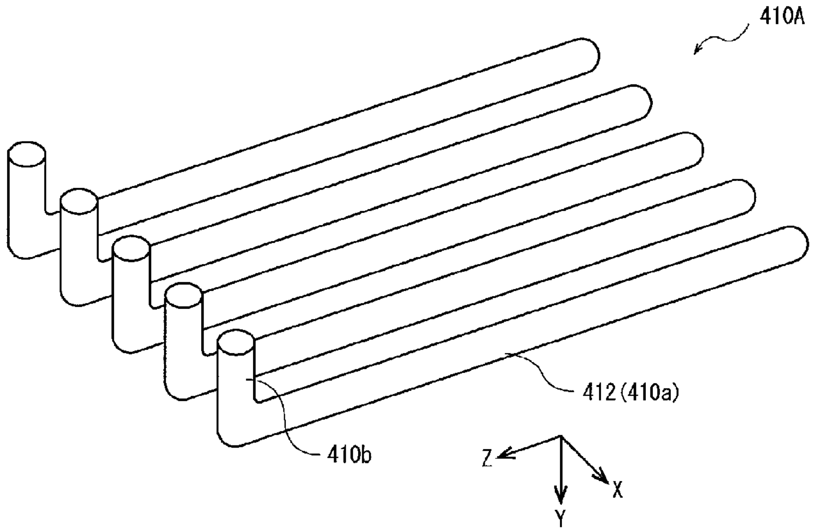
FIG. 4 is a diagram illustrating a variation of a heat pipe provided in a light illuminating apparatus according to a first embodiment of the present disclosure.

Also, although the heat pipe 410 of this embodiment is a plate-shaped member having a pipe-shaped internal space, the present disclosure is not limited thereto. FIG. 4 is a diagram illustrating a variation of the heat pipe 410 of this embodiment. A heat pipe 410A according to this variation is different from the heat pipe 410 of this embodiment in that the heat pipe 410A includes a plurality of rod-shaped heat pipes 412 extending in the Z-axis direction, instead of the space 410_z_ (FIG. 3). Similar to the heat pipe 410 of this embodiment, each rod-shaped heat pipe 412 is bent in the shape of letter L such that the substrate 205 side end part conforms to the other surface of the support plate 107, and has the bent part 410*b* parallel to the X-Y planes. Also, the rod-shaped heat pipes 412 are arranged in the X-axis direction at a predetermined interval, and have the planar part 410*a* parallel to the X-Z planes. By this configuration, as a working fluid moves in the rod-shaped heat pipes 412, similar to the heat pipe 410 of this embodiment, heat is transferred in the Z-axis direction (the opposite direction to the direction in which UV light is emitted) from the bent part 410*b*. Also, in this variation, because it is difficult to form the heat radiation fins 430*a* directly on the rod-shaped heat pipes 412, for example, a connecting plate (not shown) which connects each rod-shaped heat pipe 412 in the X-axis direction is installed, and the heat radiation fins 430*a* are installed on the corresponding connecting plate.

Second Embodiment

Figure 5:
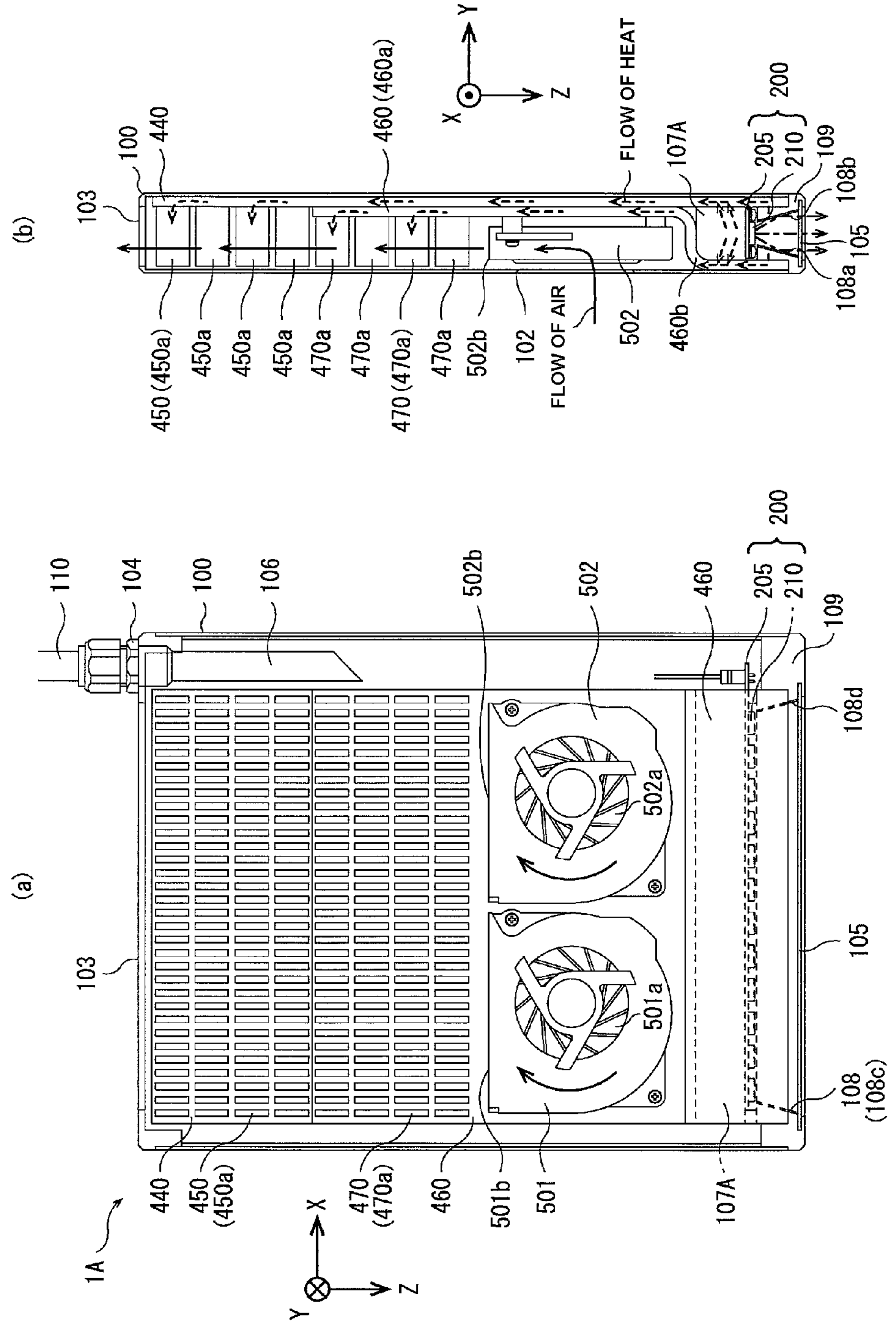
FIG. 5 is a diagram illustrating the internal structure of a light illuminating apparatus according to a second embodiment of the present disclosure.

FIG. 5 is a diagram illustrating the internal structure of a light illuminating apparatus 1A according to a second embodiment of the present disclosure, and FIG. 5(*a*) is a front projection diagram of the light illuminating apparatus 1A when viewed from the front. Also, FIG. 5(*b*) is a side projection diagram of the light illuminating apparatus 1A when viewed from the right side. Also, in FIG. 5(*b*), the internal wiring cable 106 of FIG. 5(*a*) has been omitted for clarity.

As shown in FIG. 5, the light illuminating apparatus 1A of this embodiment is different from the light illuminating apparatus 1 of the first embodiment in that the light illuminating apparatus 1A has a support member 109 to support the reflection member 108 and the window 105, and two heat pipes 440 and 460. Also, the light illuminating apparatus 1A of this embodiment is different from the light illuminating apparatus 1 of the first embodiment in that a support block 107A of this embodiment is thicker than the support plate 107 of the first embodiment and is formed in square pillar shape.

The support member 109 is a member placed to form the bottom of the case 100. The support member 109 has a square pillar shape extending along the X-axis direction, and is formed of metal having high thermal conductivity (e.g., copper and aluminum). The support member 109 has an opening 109*a* at an area facing the twelve LED devices 210, and is configured to emit UV light from each LED device 210 through the opening 109*a*. The opening 109*a* has four tapered surfaces spreading outward in the emission direction of UV light (i.e., Z-axis direction), and each mirror surface 108*a*, 108*b*, 108*c* and 108*d* is arranged on each tapered surface by inserting the reflection member 108 into the opening 109*a*. Also, the window 105 is attached to the end side (the lower side in FIGS. 5(*a*) and (*b*)) of the support member 109. Similar to the first embodiment, UV light emitted from each LED device 210 is incident on each mirror surface 108*a*, 108*b*, 108*c* and 108*d* and the window 105 of the support member 109, and because each mirror surface 108*a*, 108*b*, 108*c* and 108*d* and the window 105 increase in temperature when exposed to UV light, in this embodiment, heat from each mirror surface 108*a*, 108*b*, 108*c* and 108*d* and the window 105 is transferred to the heat pipes 440 and 460 quickly by the support member 109 (described in detail later).

As shown in FIG. 5(*b*), the support block 107A of this embodiment is thicker than the support plate 107 of the first embodiment, and is formed in the shape of a square pillar. Thus, the support block 107A of this embodiment has larger heat capacity than the heat capacity of the support plate 107 of the first embodiment, and is configured to act as a sort of heat sink. That is, heat emitted from each LED device 210 is transferred by conduction to the support block 107A through the substrate 205 quickly.

Also, as shown in FIG. 5(*b*), the light illuminating apparatus 1A of this embodiment has the two heat pipes 440 and 460 arranged in an overlapping manner. The heat pipes 440 and 460 have the same configuration and function as the heat pipe 410 of the first embodiment, only different in shape.

The heat pipe 440 is a plate-shaped member disposed along the rear side inner surface of the case 100. One end side of the heat pipe 440 (the lower side in FIGS. 5(*a*) and (*b*)) is bonded to the support member 109 and the support block 107A, and as indicated by dotted arrows in FIG. 5(*b*), heat conducted from them is transferred to the other end side (the upper side in FIGS. 5(*a*) and (*b*)). A plurality of heat radiation fins 450*a* of a heat sink 450 is welded to the other end side of the heat pipe 440 (the upper side in FIGS. 5(*a*) and (*b*)) on one side surface of the heat pipe 440 (the surface of the side where bonding to the support member 109 and the support block 107A is made). Each heat radiation fin 450*a* is installed erect to protrude in the Y-axis direction from one side surface of the heat pipe 440 and radiates the heat transferred to the heat pipe 440 in the air, similar to the heat radiation fins 430*a* of the first embodiment.

The heat pipe 460 is a member having a planar part 460*a* and a bent part 460*b*. The planar part 460*a* is a plate-shaped part extending in the Z-axis direction from the top of the support block 107A (the centrifugal fans 501 and 502 side surface) toward the heat radiation fins 450*a*, and is bonded to one side surface of the heat pipe 440 such that the planar part 460*a* is in close contact with one side surface of the heat pipe 440. The bent part 460*b* is a part which is bent to conform to the top and the front of the support block 107A (the surface of the opposite side to the surface where bonding to the heat pipe 440 is made), and is bonded to the support member 109 and the support block 107A. Also, as indicated by dotted arrows in FIG. 5(*b*), heat conducted from them is transferred to the planar part 460*a*. A plurality of heat radiation fins 470*a* of a heat sink 470 is welded to the planar part 460*a* of the heat pipe 460 on one side surface of the heat pipe 460 (the surface of the opposite side to the surface where bonding to the heat pipe 440 is made). Similar to the heat radiation fins 450*a*, each heat radiation fin 470*a* is installed erect to protrude in the Y-axis direction from one side surface of the heat pipe 460, and radiates the heat transferred to the heat pipe 460 in the air.

As described above, in this embodiment, the support member 109 and the support block 107A are inserted by one end part of the heat pipe 440 and the bent part 460*b* of the heat pipe 460, and heat from the support member 109 and the support block 107A is efficiently transferred by the two heat pipes 440 and 460, thereby impeding a temperature rise of the support member 109 and the support block 107A. That is, heat generated from each LED device 210 and transferred to the support block 107A through the substrate 205 is efficiently transferred by the two heat pipes 440 and 460. Also, each mirror surface 108*a*, 108*b*, 108*c* and 108*d* and the window 105 generate heat by UV light as described above, and the heat is efficiently transferred by the two heat pipes 440 and 460 through the support member 109. Also, the heat transferred by the two heat pipes 440 and 460 is efficiently radiated in the air from each heat radiation fin 450*a* and each heat radiation fin 470*a*.

As described above, in this embodiment, similar to the first embodiment, the case 100 and the heat pipes 440 and 460 form a sort of wind tunnel to define a space in which an air current flows, thereby efficiently cooling each heat radiation fin 450*a* and 470*a*. Also, in this embodiment, the two heat pipes 440 and 460 are configured to overlap, so that the Z-axis direction length of the planar part 460*a* of the heat pipe 460 is shorter than the Z-axis direction length of the heat pipe 440, and thus, an area for forming the heat radiation fins 450*a* on the heat pipe 440 is provided, and an area for forming the heat radiation fins 470*a* on the heat pipe 460 is provided. Also, similar to the first embodiment, a thickness reduction of the light illuminating apparatus 1A is achieved while efficiently cooling each heat radiation fin 450*a* and 470*a* by the centrifugal fans 501 and 502.

Third Embodiment

Figure 6:
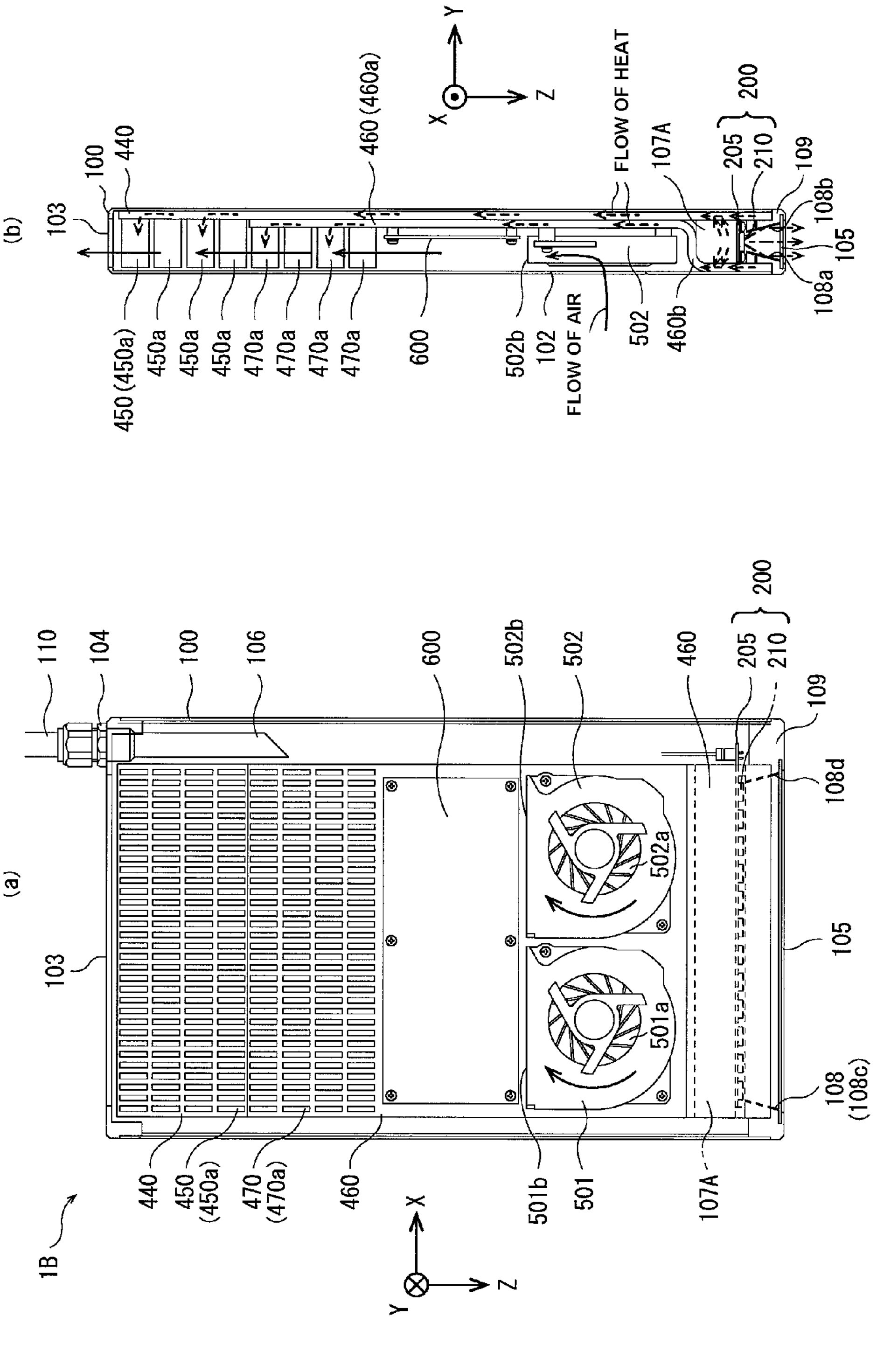
FIG. 6 is a diagram illustrating the internal structure of a light illuminating apparatus according to a third embodiment of the present disclosure.

FIG. 6 is a diagram illustrating the internal structure of a light illuminating apparatus 1B according to a third embodiment of the present disclosure, and FIG. 6(*a*) is a front projection diagram of the light illuminating apparatus 1B when viewed from the front. Also, FIG. 6(*b*) is a side projection diagram of the light illuminating apparatus 1B when viewed from the right side. Also, in FIG. 6(*b*), the internal wiring cable 106 of FIG. 6(*a*) has been omitted for clarity.

As shown in FIG. 6, the light illuminating apparatus 1B of this embodiment is different from the light illuminating apparatus 1A of the second embodiment in that the light illuminating apparatus 1B has an LED driving circuit 600 in a space between the centrifugal fans 501 and 502 and the heat radiation fins 470*a*.

The LED driving circuit 600 is a circuit which is electrically connected to the internal wiring cable 106 and the substrate 205 to control a drive current supplied to each LED device 210. As shown in FIG. 6, the LED driving circuit 600 of this embodiment is disposed in the space between the centrifugal fans 501 and 502 and the heat radiation fins 470*a*. Thus, the LED driving circuit 600 is efficiently cooled by the air flowing from the centrifugal fans 501 and 502 toward the heat radiation fins 470*a*.

Fourth Embodiment

Figure 7:
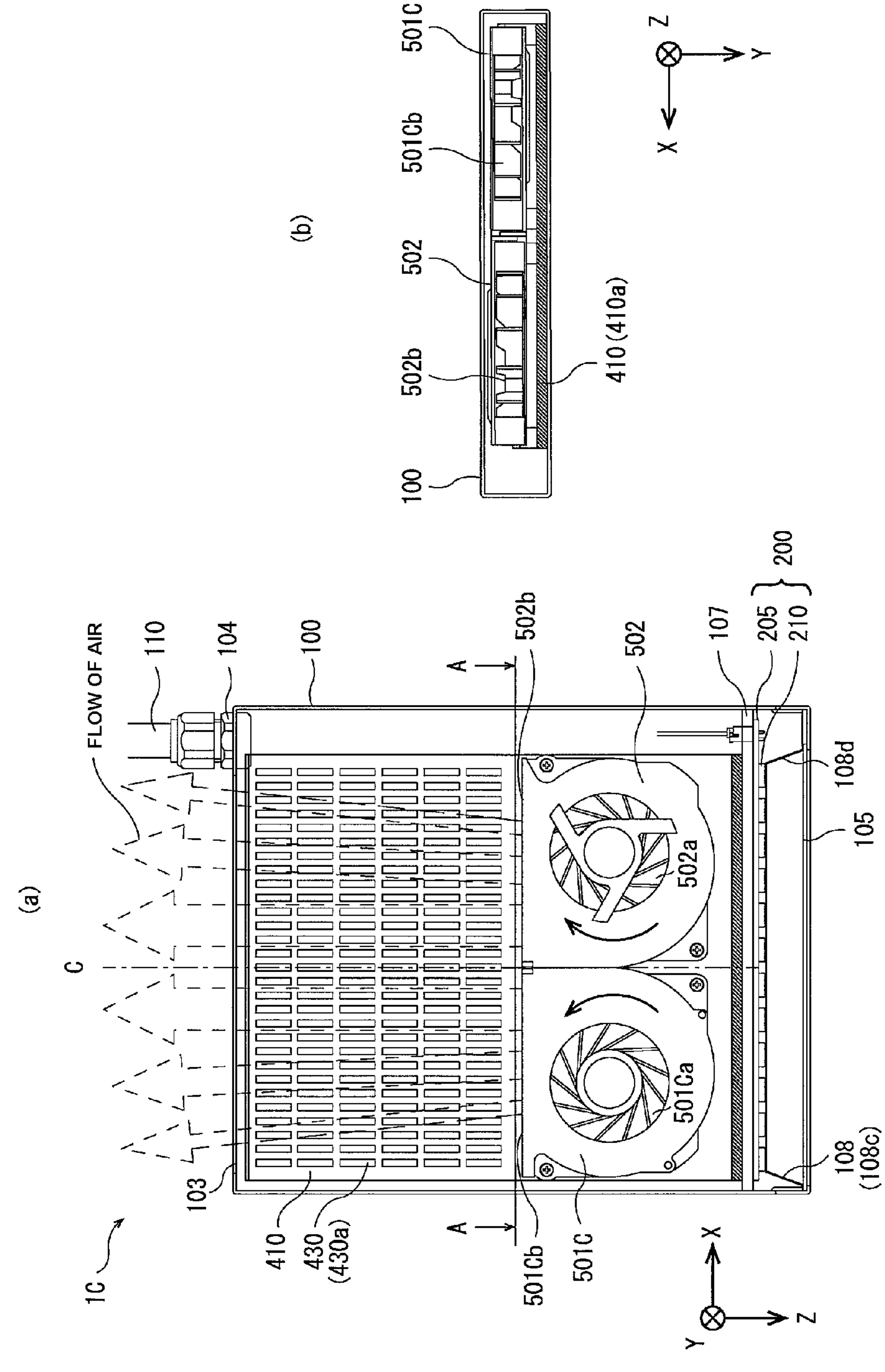
FIG. 7 is a diagram illustrating the internal structure of a light illuminating apparatus according to a fourth embodiment of the present disclosure.

FIG. 7 is a diagram illustrating the internal structure of a light illuminating apparatus 10 according to a fourth embodiment of the present disclosure, and FIG. 7(*a*) is a front projection diagram of the light illuminating apparatus 10 when viewed from the front. Also, FIG. 7(*b*) is a cross-sectional view of FIG. 7(*a*) taken along A-A.

As shown in FIG. 7, the light illuminating apparatus 10 of this embodiment is different from the light illuminating apparatus 1 of the first embodiment in that the light illuminating apparatus 10 has a centrifugal fan 501C rotating in the counterclockwise direction.

The centrifugal fan 501C is a centrifugal sirocco fan having the same configuration as the centrifugal fan 502, only different in rotation direction, and the centrifugal fans 501C and 502 push the air taken from the outside in the centrifugal direction (i.e., rotation direction) to generate an air current in the case 100. In the centrifugal fans 501C and 502 of this configuration, there is a problem with a difference in direction and amount of wind in the horizontal direction (i.e., X-axis direction) of air exhaust ports 501Cb and 502*b*. Thus, in this embodiment, using the centrifugal fan 501C and the centrifugal fan 502 of different rotation directions, air is allowed to be sent approximately uniformly in the horizontal direction of the heat pipe 410. Specifically, when viewed from the front (FIG. 7(*a*)), the centrifugal fan 501C rotating in the counterclockwise direction is disposed on the left side of the centerline C of the heat pipe 410, and is configured to send air from the centrifugal fan 501C to each heat radiation fin 430*a* disposed on the left side of the centerline C. Also, the centrifugal fan 502 is disposed on the right side of the centerline C of the heat pipe 410, and is configured to send air from the centrifugal fan 502 to each heat radiation fin 430*a* disposed on the right side of the centerline C. By this configuration, air is sent symmetrically with respect to the heat radiation fins 430*a* disposed on the left and right sides with the centerline C of the heat pipe 410 interposed in between, thereby achieving symmetrical cooling on the left and right sides.

Fifth Embodiment

Figure 8:
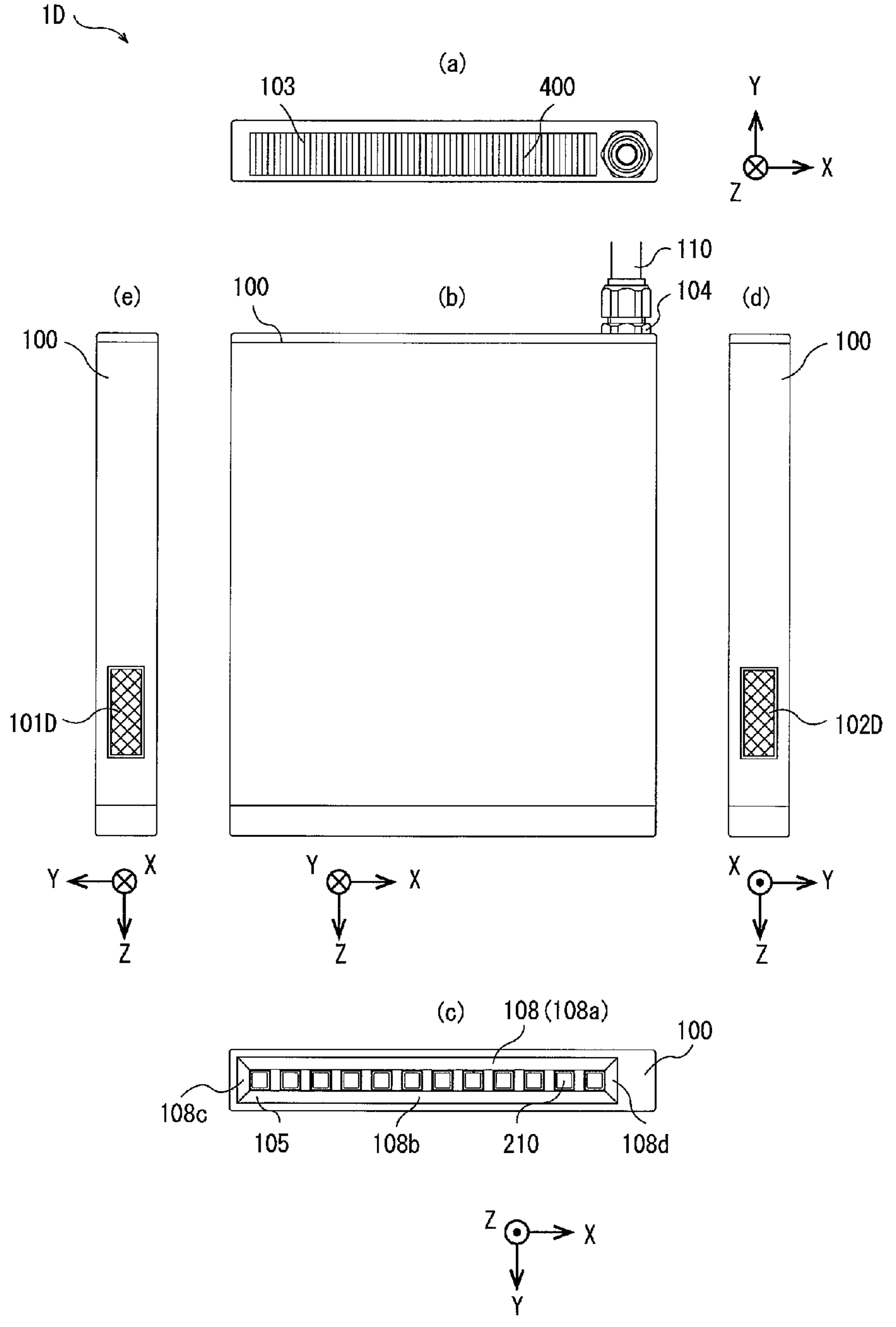
FIG. 8 is a diagram illustrating the appearance of a light illuminating apparatus according to a fifth embodiment of the present disclosure.

FIG. 8 is a diagram illustrating the appearance of a light illuminating apparatus 1D according to a fifth embodiment of the present disclosure, and FIG. 8(*a*) is a top view of the light illuminating apparatus 1D. Also, FIG. 8(*b*) is a front view of the light illuminating apparatus 1D, and FIG. 8(*c*) is a bottom view of the light illuminating apparatus 1D. Also, FIG. 8(*d*) is a right side view of the light illuminating apparatus 1D, and FIG. 8(*e*) is a left side view of the light illuminating apparatus 1D. Also, FIG. 9 is a diagram illustrating the internal structure of the light illuminating apparatus 1D, and is a front projection diagram of the light illuminating apparatus 1D when viewed from the front.

Figure 9:
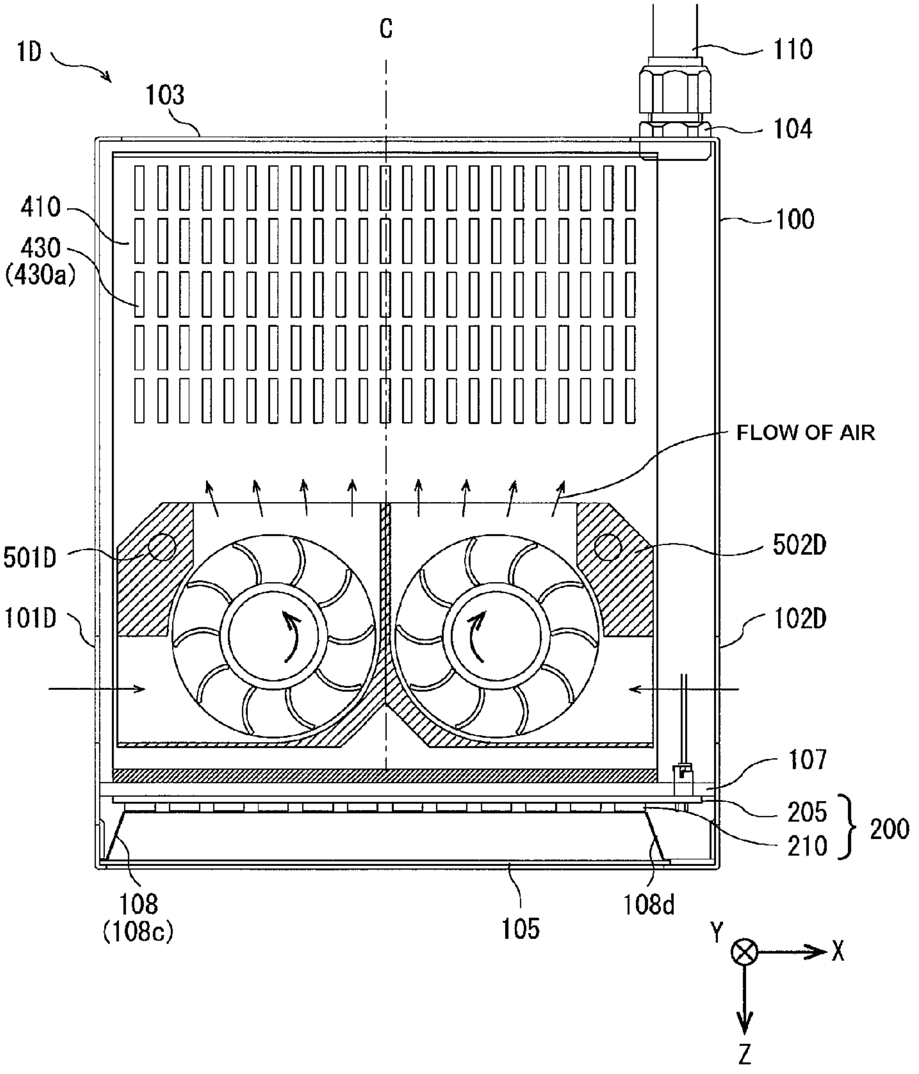
FIG. 9 is a diagram illustrating the internal structure of a light illuminating apparatus according to a fifth embodiment of the present disclosure.

As shown in FIGS. 8 and 9, the light illuminating apparatus 1D of this embodiment is different from the light illuminating apparatus 10 of the fourth embodiment in that the light illuminating apparatus 1D has centrifugal turbo fans 501D and 502D, an air intake port 101D of the centrifugal turbo fan 501D is formed on the left side surface of the case 100 (FIG. 8(*e*)), and an air intake port 102D of the centrifugal turbo fan 502D is formed on the right side surface of the case 100 (FIG. 8(*d*)).

The centrifugal turbo fans 501D and 502D are a so-call cross-flow fan, and take in the outside air from the air intake ports 101D and 102D respectively and send the air to each heat radiation fin 430*a*. Also, in this embodiment, similar to the fourth embodiment, the centrifugal turbo fan 501D disposed on the left side when viewed from the front (FIG. 9) is configured to rotate in the counterclockwise direction, the centrifugal turbo fan 502D disposed on the right side when viewed from the front (FIG. 9) is configured to rotate in the clockwise direction, and as the heat radiation fins 430*a* are disposed closer to the centerline C of the heat pipe 410, a larger amount of air is sent and efficient cooling can be thereby achieved.

Further, it should be appreciated that the embodiments disclosed herein are illustrative in all aspects, but not limitative. The scope of the present disclosure is defined by the appended claims, but not the above description, and is intended to include all modifications within the claims and the meaning and scope of equivalents thereof.

The invention claimed is:

1. A light illuminating apparatus for illuminating light in line shape extending in a first direction on an illumination surface, the light illuminating apparatus comprising:

an elongated substrate extending in the first direction;

a plurality of light emitting diode (LED) light sources placed and arranged on a surface of the substrate at a preset interval along the first direction, and configured to emit the light in line shape;

a heat transfer means of which at least a part is in contact with the substrate, the heat transfer means extending in a second direction perpendicular to the first direction from the substrate, and configured to transfer heat generated from the LED light sources in the second direction;

a heat radiation means having a plurality of heat radiation fins protruding in a third direction perpendicular to the first direction and the second direction from the heat transfer means and installed to extend in the second direction;

an illuminator having a box shape and configured to house the substrate, the heat transfer means and the heat radiation means and to form a wind tunnel at an area in which the heat radiation means is formed; and a centrifugal fan located in the second direction between the substrate and the heat radiation means, and configured to draw air from outside the illuminator into the wind tunnel to generate an air current in the second direction within the wind tunnel.

2. The light illuminating apparatus according to claim 1, wherein the illuminator has an air intake port on at least one of a first surface facing an imaginary surface formed by the ends of the plurality of heat radiation fins and a second surface facing the first direction so as to intake air along the first direction, the air intake port configured to take in air from outside the illuminator, and the centrifugal fan takes in air from the air intake port.

3. The light illuminating apparatus according to claim 1, wherein the first direction width of the heat transfer means is approximately equal to the first direction width of the substrate.

4. The light illuminating apparatus according to claim 1, wherein a bottom part of the heat transfer means is bent in a shape of letter L, and the bottom part is thermally coupled with a rear surface of the substrate opposite the surface on which the plurality of LED light sources are arranged.

5. The light illuminating apparatus according to claim 1, wherein the light illuminating apparatus further comprises a support block which is thermally coupled with a rear surface of the substrate opposite the surface on which the plurality of LED light sources are arranged and supports the substrate, the heat transfer means comprises a first heat transfer means, and a second heat transfer means smaller than the first heat transfer means in the second direction, the heat radiation means comprises a first heat sink having the heat radiation fins on the first heat transfer means, and a second heat sink having the heat radiation fins on the second heat transfer means, and the support block is located by a bottom part of the first heat transfer means and a bottom part of the second heat transfer means.

6. The light illuminating apparatus according to claim 1, wherein a driving circuit is provided between the centrifugal fan and the heat radiation means to drive the LED light sources.

7. The light illuminating apparatus according to claim 1, wherein the heat transfer means comprises a plate-shaped heat pipe extending in the first direction and the second direction.

8. The light illuminating apparatus according to claim 1, wherein the heat transfer means comprises a plurality of rod-shaped heat pipes arranged in the first direction and extending in the second direction.

9. The light illuminating apparatus according to claim 1, wherein the substrate is placed on a plane defined by the first direction and the third direction, and optic axes of each of the LED light sources face an opposite direction to the second direction.

10. The light illuminating apparatus according to claim 9, wherein the LED light sources are arranged in N rows along the third direction when the substrate is planarized, in which N is an integer larger than or equal to 2.

11. The light illuminating apparatus according to claim 1, wherein the substrate is placed on a plane defined by the first direction and the second direction, and optic axes of each of the LED light sources face the third direction.

12. The light illuminating apparatus according to claim 11, wherein the LED light sources are arranged in N rows along the second direction when the substrate is planarized, in which N is an integer larger than or equal to 2.

13. The light illuminating apparatus according to claim 1, wherein the centrifugal fan comprises a first centrifugal fan having a fan which rotates in a counterclockwise direction, and a second centrifugal fan having a fan which rotates in a clockwise direction, and the first centrifugal fan and the second centrifugal fan are placed and arranged side-by-side in the first direction.

14. The light illuminating apparatus according to claim 1, wherein the light is light including a wavelength used for an ultraviolet curing resin.

* * * * *